United States Patent
Bellini et al.

(10) Patent No.: US 8,865,964 B2
(45) Date of Patent: Oct. 21, 2014

(54) BIOMATERIALS, THEIR PREPARATION BY ELECTROSPINNING AND THEIR USE IN THE BIOMEDICAL AND SURGICAL FIELD

(75) Inventors: Davide Bellini, Albignasego (IT); Lanfranco Callegaro, Padua (IT); Marie Astier, Agliana (IT); Fabio Giusti, La Briglia-Vaiano (IT)

(73) Assignee: ANIKA Therapeutics S.r.l., Abano Terme (IT)

( * ) Notice: Subject to any disclaimer, the term of this patent is extended or adjusted under 35 U.S.C. 154(b) by 278 days.

(21) Appl. No.: 13/056,541

(22) PCT Filed: Jul. 24, 2009

(86) PCT No.: PCT/EP2009/059535
§ 371 (c)(1),
(2), (4) Date: Jan. 28, 2011

(87) PCT Pub. No.: WO2010/012653
PCT Pub. Date: Feb. 4, 2010

(65) Prior Publication Data
US 2011/0196328 A1  Aug. 11, 2011

(30) Foreign Application Priority Data
Jul. 29, 2008 (IT) ................ FI2008A0143

(51) Int. Cl.
*A61F 13/15* (2006.01)
*A61L 27/60* (2006.01)

(52) U.S. Cl.
CPC ..................... *A61L 27/60* (2013.01)
USPC ....................................................... 604/367

(58) Field of Classification Search
USPC ....................................................... 604/367
See application file for complete search history.

(56) References Cited

U.S. PATENT DOCUMENTS

| | | | | |
|---|---|---|---|---|
| 5,520,916 A | * | 5/1996 | Dorigatti et al. | 424/402 |
| 5,622,707 A | * | 4/1997 | Dorigatti et al. | 424/402 |
| 5,824,335 A | * | 10/1998 | Dorigatti et al. | 424/443 |
| 7,083,697 B2 | * | 8/2006 | Dao et al. | 156/167 |
| 7,166,570 B2 | * | 1/2007 | Hunter et al. | 514/21.92 |
| 7,241,736 B2 | * | 7/2007 | Hunter et al. | 424/85.1 |
| 7,661,541 B2 | * | 2/2010 | Dao et al. | 210/500.22 |
| 8,246,576 B2 | * | 8/2012 | Slager | 604/103.02 |
| 8,256,233 B2 | * | 9/2012 | Boyden et al. | 62/66 |
| 8,268,968 B2 | * | 9/2012 | Ooya et al. | 530/354 |
| 2004/0018226 A1 | * | 1/2004 | Wnek et al. | 424/443 |
| 2007/0225631 A1 | * | 9/2007 | Bowlin et al. | 602/52 |
| 2007/0299043 A1 | * | 12/2007 | Hunter et al. | 514/171 |
| 2008/0132941 A1 | * | 6/2008 | Sullivan et al. | 606/219 |

FOREIGN PATENT DOCUMENTS

WO   93/11803 A1   6/1993

OTHER PUBLICATIONS

In Chui Um et al., "Electro-Spinning and Electro-Blowing of Hyaluronic Acid" Biomacromolecules, Jul. 5, 2004, 1428-1436, vol. 5, No. 4, American Chemical Society.
Ulrich Boudriot et al., "Electrospinning Approaches Toward Scaffold Engineering—A Brief Overview" Artificial Organs, Oct. 2006, 785-792, vol. 30, No. 10, Blackwell Publishing, Inc.
Wee-Eong Teo et al., "Electrospun scaffold tailored for tissue-specific extracellular matrix" Biotechnology Journal, 2006, 918-929, vol. 1, No. 9, Wiley InterScience.
International Search Report from PCT/EP2009/059535 dated May 3, 2010 (2 pages).

* cited by examiner

*Primary Examiner* — Susan Su
*Assistant Examiner* — Guy K Townsend
(74) *Attorney, Agent, or Firm* — McCormick, Paulding & Huber LLP

(57) ABSTRACT

There is described a new non-woven fabric produced with the electrospinning technique, and the use thereof as new biomaterial for the biomedical and surgical field.

18 Claims, 1 Drawing Sheet

Growth of fibroblasts on new non-woven fabric compared to Laserskin membrane

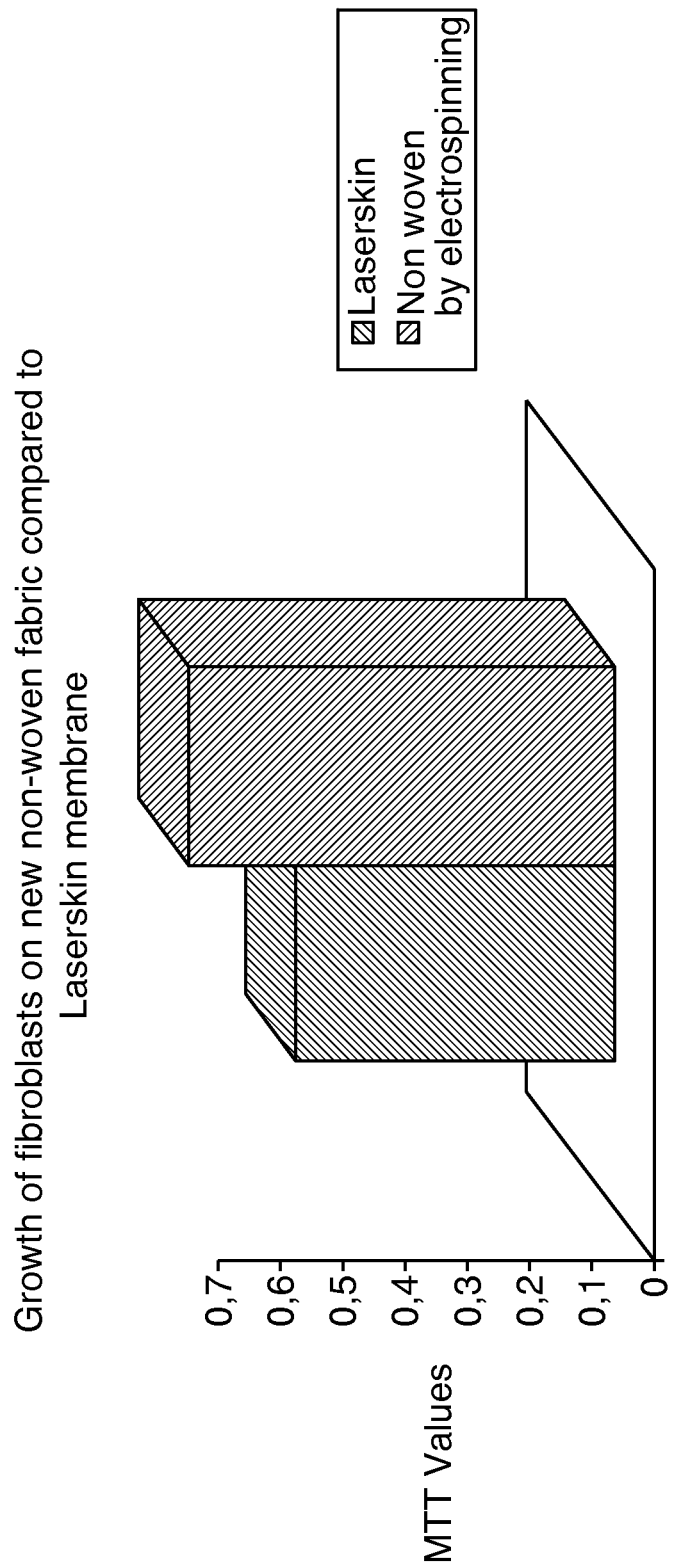

BIOMATERIALS, THEIR PREPARATION BY ELECTROSPINNING AND THEIR USE IN THE BIOMEDICAL AND SURGICAL FIELD

CROSS REFERENCE TO RELATED APPLICATIONS

This application is entitled to the benefit of and incorporates by reference essential subject matter disclosed in Italian Patent Application No. FI2008A000143 filed on Jul. 29, 2008 and International Patent Application No. PCT/EP2009/059535 filed on Jul. 24, 2009.

FIELD OF THE INVENTION

The present invention relates to the field of biomaterials produced for biomedical use, in particular of non-woven fabric, wherein fibres obtainable by the electrospinning technique are used.

STATE OF THE ART

As is known, hyaluronic acid (HA) is a heteropolysaccharide composed of alternating residues of D-glucuronic acid and N-acetyl-D-glucosamine.

It is a linear chain polymer with molecular weight that may range between 50,000 and $13 \times 10^6$ Da, according to the source it is obtained from and to the methods of preparation used.

It is found in nature in pericellular gels, in the fundamental substance of the connective tissue of vertebrate organisms (of which it is one of the main components), in vitreous humor and in the umbilical cord.

Hyaluronic acid is one of the main molecules constituting the cartilaginous matrix but it also represents the major non-proteinic component of the synovial fluid. Being a highly hydrophile viscoelastic molecule, it imparts lubricating properties to the synovial fluid and for these reasons, for over 30 years HA has been used in the pathology of ostheoarthrosis, especially for treating the pain associated therewith (Ghosh P. et al., Semin Arthritis Rheum, 2002, 32: 10-37).

In fact, at an articular level the hyaluronic acid contained in the synovial fluid also serves as a viscous lubricant during slow movements while during quick movements, with its elastic properties it absorbs any traumas or microtraumas that may affect the articulation; in pathological situations both the concentration of HA and its mean molecular weight decrease considerably, altering the physiological features of the synovial fluid.

It has also been proved that HA plays a fundamental role in the tissue healing process both from the structural point of view (in the extracellular matrix organization and in the control of its hydration) and as stimulating substance for a large number of processes wherein it intervenes either directly or indirectly (clotting, phagocyte activity, fibroblast proliferation, neovascularization, riepitelization, etc.) (Weigel P. et al., *J Theoretical Biol*, 1986:219-234; Abatangelo G. et al., *J Surg Res*, 1983, 35:410-416; Goa K. et al., *Drugs*, 1994, 47:536-566).

Such widely recognized properties have long been used for preparing dressings used for treating wounds, ulcers and skin wounds of various origin.

HA therefore plays an important role in the biological organism both as structural and mechanical support of tissues, and as active component in the physiology of tissue cells such as skin, tendons, muscles and cartilage.

Hyaluronic acid esters are, among the derivatives of HA, particularly important in the process of forming new engineered tissues, since they can be processed into different shapes for making biomaterials usable for tissue reconstruction. The use of HA derivatives for making fibres (EP 0618817 B1) is in fact known, which processed as non-woven, make up a biomaterial in the form of three-dimensional matrix (free from cellular component) usable in the dermatological field; moreover, the above three-dimensional structures may be charged with mesenchymal cells and kept in vitro for a time required for favoring the proliferation and/or the partial differentiation thereof (EP 0863776 B1), for forming new artificial tissue to be implanted in vivo.

The above biomaterials have particular biocompatibility features totally matching those of hyaluronic acid as is, but having a different biodegradability and so, when implanted in vivo, the residence time in situ is considerably higher than that of unmodified HA, thus allowing the reconstruction of the damaged tissue (Campoccia D. et al., Biomaterials, 1998, 19: 2101-2127).

The so-called Electrospinning technique is known, which allows making ultra-thin fibres through the stretching carried out by an electrical field.

A polymer solution is obtained according to this technique, using a polar solvent that may therefore make the solution conductive.

A drop of the polymer solution is introduced, generally by a needle connected to earth, inside a very strong electrical field obtained by placing a screen with a large potential difference in front of the needle itself. The drop is attracted in the form of many small drops towards the screen and a very fine spray is formed, but under certain condition of surface tension and viscosity of the solution, the drop is stretched and an immediate evaporation of the solvent occurs by the effect of the large surface it takes on, thus obtaining polymer fibres having a nanometric diameter (even 50 manometers).

It should be noted that while the literature on this technique is very large, to date it has found poor application in the industry.

BRIEF DESCRIPTION OF THE FIGURE

FIG. 1 shows the growth data of fibroblasts on the non-woven fabric according to the invention compared to a control biomaterial.

SUMMARY OF THE INVENTION

Objects of the invention are new biomaterials in the form of fibres, tissues and non-woven fabric materials comprising fibres of hyaluronic acid derivatives having diameter smaller than a micron.

DETAILED DESCRIPTION OF THE INVENTION

It has now been surprisingly found that by subjecting solutions composed of HA derivatives (in particular hyaluronic acid esters) to electrospinning it is possible to obtain fibres with a diameter below a micron that allow making biomaterials in the form of non-woven fabric or woven fabric.

HA derivatives that may be used with the electrospinning technique for making the new biomaterials object of the present invention are listed below:
1. HA salified with organic and/or inorganic bases, in particular calcium and zinc salts;
2. Hyaff®: HA esters with aliphatic, arylaliphatic, cycloaliphatic, aromatic, cyclic and heterocyclic alcohols, with an esterification percentage that may vary according to the type and length of alcohol used, from 50 to 100% (EP 0216453 B1);
3. Hyadd®: HA amides with aliphatic, arylaliphatic, cycloaliphatic, aromatic, cyclic and heterocyclic amines, with an amidation percentage from 1 to 10%, preferably 4% (EP 1095064 B1);
4. HA O-sulphated derivatives up to the 4th degree of sulfation (EP 0702699 B1);
5. Hyoxx®: HA percarboxylate derivatives obtained from the oxidation of primary oxydryl of the N-acetyl-glucosamine moiety with percarboxylation degree between 0.1 and 100%. All of the HA carboxylic groups may be salified with organic and/or inorganic bases (EP1339753).

The fibres may comprise the derivatives listed above and in particular, esters of HA, used singularly or in combination, or they may be composed of esters of HA associated with esters of alginic acid or other natural, semi-synthetic or synthetic polymers. The woven fabric and the non-woven fabric prepared by the electrospinning technique may contain a single type of fibre or it may consist of different fibres consisting of various polymers. Therefore, the subject biomaterials may comprise fibres consisting of at least an HA ester or esters of HA in combination with another polymer, or woven and non-woven fabrics with fibres at least 1% made of HA esters and for the rest consisting of other polymers.

Natural polymers that may be selected as components of the new biomaterial comprise collagen, hyaluronic acid, cellulose, chitin, chitosan, pectin, pectic acid, agar, agarose, gellan, alginic acid, starch, natural gum and polyglycan.

Semi-synthetic polymers comprise cross-linked collagen and hyaluronic acid, and chemically modified derivatives of the natural polymers listed above.

Synthetic polymers comprise polylactic acid, polyglycolic acid, copolymers of polylactic and polyglycolic acid, polycaprolacton and polyurethane.

According to the invention, by esters of hyaluronic acid it is preferably meant esters of hyaluronic acid with aromatic alcohols and in particular, benzyl ester (Hyaff 11) with a % of esterification comprised between 50 and 100%, preferably benzyl ester with a % of esterification comprised between 50-75% and 80-100%.

A further object of the present invention is the improvement of the process of preparation of the new biomaterials by electrospinning of Hyaff 11 derivatives having a % of esterification comprised between 50-75%, in fact the powders of said derivatives are insoluble in the hereinafter reported solvents and therefore the Hyaff esterified from 50-75% would be not usable for the preparation of biomaterials by electrospinning. However the Applicant surprisingly found that it is possible to solubilise, and therefore to stretch/work in an electric field, mixtures comprising Hyaff esterified 50-75% when the Hyaff is mixed up with polyvinylpirrolidone (PVP) in a w/w rate of 80:20 and preferably 87/13.

Moreover it is possible to prepare solutions comprising Hyaff 11 esterified 80-100% without mixing with PVP since they are perfectly soluble in the hereinafter reported solvents. The advantages in using Hyaff 11 partially esterified are various, in particular they give the possibility of working a polysaccharide in the wanted form of biomaterial, choosing the preferred degradation time in vivo, and therefore the time of permanence in situ, in a way dependent on the kind of tissue which must be reconstructed: a longer time for cartilaginous or bone tissues and shorter for skin tissues.

Solvents for preparing the solutions to be subjected to electrospinning according to the invention are normally selected from 1,1,1,3,3,3-hexafluoro-2-isopropanol and mixtures in all proportions of dimethyl sulfoxide and 1,1,1,3,3,3-hexafluoro-2-isopropanol and dimethylformamide (DMF) in admixture with 1,1,1,3,3,3-hexafluoro-2-isopropanol.

The concentrations of the solutions preferably of hyaluronic acid ester, according to the invention, are normally comprised between 0.01 and 200 g/L, preferably between 10 and 50 g/L, more preferably between 15 and 30 g/L.

The fibres are manufactured starting from the above solutions as described above in the comment to the state of the art.

Preferably, according to the invention the distances between the polymer source and the fibre collection plane is comprised between 1 and 50 cm, preferably between 10 and 15 cm, and the high voltage values are comprised between 1 and 160 kV, preferably between 40 and 60 kV.

The fibres thus obtained normally have a diameter comprised between 0.01 µm and 1.0 µm, preferably of 0.1 µm.

Woven and non-woven fabric sheets are prepared with the fibres thus made essentially according to the prior art. Moreover it is possible to coat synthetic devices in order to increase their bio-compatibility in vivo.

In particular, the fibres are evenly and randomly laid on the collection plane thanks to the strength of the electrical field received, and the make thereof takes place in the same electrical field. The fibres make a non-woven fabric thanks to the adherence of the fibres to each other and to the possible presence of traces of residual solvent that afterwards are eliminated. The fibres deposited according to a predefined drawing allow to obtain a bio-material in the form of woven fabric.

The collection is made on a plane, connected to earth, which may either be stationary or rotating, and with different shapes.

The new biomaterials object of the present invention substantially differ from the woven fabrics and non-woven fabrics according to the prior art for the reasons listed below:
1. triple increase of the contact surface area with the in vivo tissue treated, the weight of the subject biomaterial being equal to that of reference/control according to the prior art;
2. greater compactness and thus smaller volume, the surface unit being equal compared to the reference/control biomaterial;
3. considerable increase of wettability (up to 5 times) compared to the reference/control biomaterial;
4. bi-dimensional cell growth;
5. considerable increase of cellular proliferation compared to a control growth carried out on reference material, consisting of the same derivative processed in the shape of a membrane for ensuring a bi-dimensional proliferation like the new subject biomaterials.

To prove what stated, the Applicant has run comparative tests (described below) using a non-woven fabric based on a benzyl ester of HA having 100% esterification produced with an electrospinning technique, compared to the biomaterial called Hyalomatrix®, composed of benzyl ester of HA with 100% esterification, also processed as a non-woven fabric, and Laserskin®, holey membrane of benzyl ester of HA with 100% esterification. Hyalomatrix® is a three-dimensional matrix used by the man skilled in the art especially for the absorption of the exudate present in burns and/or in skin wounds, whereas Laserskin® is a known bi-dimensional support used for the growth of fibroblasts in the bioengineered regeneration of derma/skin.

Comparison of the absorption and wettability properties of the new non-woven fabric produced with the electrospinning technique with Hyalomatrix®

The test is run on a number of 5 pieces for each product and for each test required.

The test is run with the same surface of the two products (2×2 cm) and for surface unit with the same weight of the product.

The solvent for running the test is a sterile saline (sodium chloride 0.9%).

The results are shown in the table.

|  | Absorption with the same surface | Absorption with the same weight | Wettability |
|---|---|---|---|
| Hyalomatrix® | 1st test: 9 fold the dry weight | 1st test: 10 fold the dry weight | 1st test: 2 fold the dry weight |
|  | 2nd test: 8 fold the dry weight | 2nd test: 10 fold the dry weight | 2nd test: 2 fold the dry weight |
|  | 3rd test: 10 fold the dry weight | 3rd test: 9 fold the dry weight | 3rd test: 2.5 fold the dry weight |
|  | 4th test: 10 fold the dry weight | 4th test: 11 fold the dry weight | 4th test: 2 fold the dry weight |
|  | 5th test: 9 fold the dry weight | 5th test: 9 fold the dry weight | 5th test: 2.5 fold the dry weight |
| Non-woven fabric (produced with the electrospinning technique) | 1st test: 8 fold the dry weight | 1st test: 9 fold the dry weight | 1st test: 8 fold the dry weight |
|  | 2nd test: 8 fold the dry weight | 2nd test: 9 fold the dry weight | 2nd test: 8 fold the dry weight |
|  | 3rd test: 9 fold the dry weight | 3rd test: 8 fold the dry weight | 3rd test: 9 fold the dry weight |
|  | 4th test: 8 fold the dry weight | 4th test: 9 fold the dry weight | 4th test: 10 fold the dry weight |
|  | 5th test: 9 fold the dry weight | 5th test: 8 fold the dry weight | 5th test: 9 fold the dry weight |

The tests run on the wettability of materials follow a procedure that requires the placement of the material inside a container (Petri dish) and adding a known amount of saline. The products should not be moved for any reason.

For the absorption test, applying the same sample treatment procedure as described for wettability, the sample may be moved for favoring the imbibition thereof.

Results: while for the new non-woven fabric object of the present invention the absorption values match those of wettability, for the Hyalomatrix® non-woven fabric, which represents the state of the art, it is clear that wettability tests are about 4 times lower than both the Hyalomatrix® absorption values and the wettability test of the new biomaterial. Moreover, it is important to point out that the product weight being equal, the new non-woven fabric has a contact surface area 3 times larger than that of the known product.

This datum is very important since, the dry weight of the product being equal, an absorbing surface is obtained that is 3 times larger that allows, for example, a greater absorption of the exudate of a burn and/or skin wound than the products known in the art, without the need of compressing the wound with the selected dressing.

Example: non-woven fabric from electrospinning: dry weight: 30 mg, surface: 6 cm$^2$, absorption for wettability (without compression): 8 to 10 fold the dry weight, therefore: 240-300 mg.

Hyalomatrix® non-woven fabric: dry weight: 30 mg, surface: 3 fold less than the above, thus: 2 cm$^2$, absorption for wettability (without compression): 2 to 2.5 fold the dry weight, therefore: 60-75 g. End result: the dry weight being equal, the new dressing absorbs an amount of exudate 4 times higher with a surface 3 times larger without compression of the wound or of the burn treated.

Assessment of the cellular viability of human fibroblasts seeded on the new non-woven product made with the electrospinning technique compared to Laserskin®, holey membrane of benzyl ester of HA Experimental rationale: Human fibroblasts were seeded at a density of 500,000 cell/cm$^2$ on 1 cm×1 cm pieces of tested materials.

At 7 days the samples were subject to MTT test for assessing the cellular viability.

Materials and Methods

Fibroblast Preparation

Dermic fibroblasts were collected, upon informed consent, from subjects undergoing a surgery that had no alterations of the connective tissue. The isolated fibroblasts from biopsies were grown in DMEM containing 10% FCS. Fibroblasts between the third and the sixth step were seeded at a density of 500.000 per cm$^2$ of the biomaterials described above. The above biomaterials were kept for 7 days at 37° C. in an atmosphere of 95% air and 5% CO2.

The culture medium is added with ascorbic acid 50 µg/ml. Test MTT: tetrazolium salt subject to redox reaction only by the mitochondrial enzymes of vital fibroblasts (Dezinot F. et al., J Immunol Methods, 1986, 22 (89): 271-277).

Briefly, the cells are incubated with a solution MTT 0.5 mg/ml for 3 hours. At the end of the incubation, the dye is extracted from the cells by an extraction solution (90% isopropanol, 10% DMSO) for the readout at 540 nm/660 nm.

Results: FIG. 1 shows the considerable increase (more than 30%) of the growth of fibroblasts on the new non-woven fabric compared to the control biomaterial. Proliferation, for the compactness of the new substrate, takes place in two dimensions, whereas the non-woven fabric Hyalomatrix®, known in the art, only shows a three-dimensional proliferation and for this reason a membrane, Laserskin®, wherein the cell proliferation takes place in two dimensions, was used as control/comparison matrix. Thanks to the compactness of the new biomaterial, related to the thickness of its fibres, it was possible to prepare non-woven fabrics that appear like porous surfaces whereon the fibroblasts can "anchor" better than a smooth surface like that of a Laserskin® membrane, the substrate normally used by the man skilled in the art for the proliferation of skin cells. Therefore, the material produced according to the electrospinning technique will better favor the skin regeneration in the case it is used as treatment for skin wounds.

The new biomaterials in the form of fibre, woven fabric or non-woven fabric of the present invention may advantageously be used in various types of micro-surgeries in dermatology, odontology, stomatology, otorhinolaryngology, orthopaedics, neurosurgery and in the surgery of internal organs, wherein it is necessary to use a substance that may be metabolized by the organism and which is capable of facilitating the flap-take, the riepitelization of membrane mucosa, the stabilization of grafts and cavity filling. Moreover, they may advantageously be used as buffer means in nose and inner ear surgery, for forming/regenerating new bioengineered tissues either in association or not with differentiated or undifferentiated cells, and finally for making new advanced dressings to use in the management of burns and skin wounds (comprising ulcers of various etiology, surgical wounds and abrasions) since, as proved above, they favor the exudate absorption and skin regeneration.

The invention shall be more and better understood in the light of the following examples.

EXAMPLE 1

A solution of ester of hyaluronic acid HYAFF 11 prepared at 15 g/L in 1,1,1,3,3,3-hexafluoro-2-isopropanol is spun in an electrical field at 54 kV voltage. The fibres are formed in the space between the source and the revolving collecting cylinder, connected to earth, where afterwards they are laid for making the non-woven fabric. In this case, the distance is 15 cm.

EXAMPLE 2

A solution of ester of hyaluronic acid HYAFF 11/p75 at 30 g/L in 1,1,1,3,3,3-hexafluoro-2-isopropanol was prepared under light stirring. The obtained solution is added with polyvinylpirrolidone (PVD) in order to increase the solubility in the solvent. The preferred ratio HYAFF/PVD is 87:13.

The solution thus obtained is spun in the electrical field at a voltage value of 42 kV and a distance of 12 cm.

EXAMPLE 3

A solution of ester of hyaluronic acid HYAFF 11/p80 at 40 g/L in 1,1,1,3,3,3-hexafluoro-2-isopropanol was prepared under light stirring.

The solution thus obtained is spun in the electrical field at a voltage value of 40 kV and a distance of 12 cm.

EXAMPLE 4

A solution of ester of hyaluronic acid HYAFF 11 at 50 g/L in 1,1,1,3,3,3-hexafluoro-2-isopropanol was prepared under light stirring.

The solution thus obtained is spun in the electrical field at a voltage value of 50 kV and a distance of 12 cm.

The foregoing description of embodiments of the present invention has been presented for the purpose of illustration and description. It is not intended to be exhaustive or to limit the invention to the particular forms disclosed. Obvious modifications and variations are possible in light of the above disclosure without departing from the spirit and scope of the present invention. The embodiments described were chosen to best illustrate the principles of the invention and practical applications thereof to enable one of ordinary skill in the art to utilize the invention in various embodiments and with various modifications as suited to the particular use contemplated. It is intended that the scope of the invention be defined by the claims appended hereto.

What is claimed is:

1. Biomaterials in the form of woven or non-woven fabric comprising fibers having a diameter smaller than a micron of hyaluronic acid derivatives made of the benzyl ester of hyaluronic acid with a percentage of esterification comprised between 50-100% obtainable by electrospinning technique.

2. Biomaterials according to claim 1 wherein the percentage of esterification is between 80% and 100%.

3. Biomaterials according to claim 1 wherein the percentage of esterification is 100%.

4. Biomaterials according to claim 1 wherein the woven or non-woven fabric consists of the benzyl ester of hyaluronic acid.

5. Biomaterials according to claim 4 wherein the percentage of esterification is between 80% and 100%.

6. Biomaterials according to claim 4 wherein the percentage of esterification is 100%.

7. Biomaterials according to claim 1 wherein said fibres have diameter comprised between 0.01 μm and 1.0 μm.

8. Biomaterials according to claim 7 wherein said fibres have diameter of 0.1 μm.

9. Biomaterials according to claim 1 wherein said fibres are used in combination or associated with esters of alginic acid or other natural, semi-synthetic or synthetic polymers.

10. Biomaterials according to claim 1 consisting of a single type of fibres or of different fibres consisting of various polymers.

11. Biomaterials according to claim 10 comprising fibres consisting of at least fibres of HA benzyl ester with a % of esterification comprised between 50-100% in combination with another polymer or fibres consisting of at least 1% of HA esters and the remained consisting of natural, semi-synthetic or synthetic polymers.

12. Biomaterials according to claim 11 wherein said natural polymers are chosen among: collagen, hyaluronic acid, cellulose, chitin, chitosan, pectin, pectic acid, agar, agarose, gellan, alginic acid, starches, natural gums, polyglycans.

13. Biomaterials according to claim 11 wherein said semi-synthetic polymers are chosen among: cross-linked collagen and hyaluronic acid and chemically modified derivatives of collagen, hyaluronic acid, cellulose, chitin, chitosan, pectin, pectic acid, agar, agarose, gellan, alginic acid, starches, natural gums, or polyglycans.

14. Biomaterials according to claim 11 wherein said synthetic polymers are chosen among: polylactic acid, polyglycolic acid, copolymers of polylactic and polyglycolic acid, polycaprolacton and polyurethane.

15. Use of biomaterials or fibres according to claim 1 or the preparation of coatings, medication tools and/or bioengineered biomaterials.

16. Use of biomaterials or fibres according to claim 1 for the absorption of the exudate present in burns and/or in skin wounds or for the growth of fibroblasts in the regeneration of derma/skin.

17. Use of biomaterials or fibres according to claim 1 in dermatology, odontology, stomatology, otorhinolaryngology, orthopaedics, neurosurgery and in the surgery of internal organs.

18. Use of biomaterials or fibres according to claim 1 as tampons in the surgical treatment of nose and ears.

* * * * *